(12) United States Patent
Kim et al.

(10) Patent No.: US 9,370,595 B2
(45) Date of Patent: Jun. 21, 2016

(54) OLFACTORY DISPLAY

(75) Inventors: Dong Wook Kim, Tokyo (JP); Hiroshi Ando, Tokyo (JP)

(73) Assignee: National Institute of Information and Communications Technology, Tokyo (JP)

(*) Notice: Subject to any disclaimer, the term of this patent is extended or adjusted under 35 U.S.C. 154(b) by 350 days.

(21) Appl. No.: 14/001,081

(22) PCT Filed: Jul. 27, 2012

(86) PCT No.: PCT/JP2012/069193
§ 371 (c)(1),
(2), (4) Date: Aug. 22, 2013

(87) PCT Pub. No.: WO2013/121606
PCT Pub. Date: Aug. 22, 2013

(65) Prior Publication Data
US 2013/0327848 A1    Dec. 12, 2013

(30) Foreign Application Priority Data
Feb. 15, 2012    (JP) .................................. 2012-030611

(51) Int. Cl.
*B01F 3/04* (2006.01)
*A61L 9/12* (2006.01)
*F04B 43/04* (2006.01)

(52) U.S. Cl.
CPC . *A61L 9/12* (2013.01); *A61L 9/125* (2013.01); *B01F 3/04* (2013.01); *F04B 43/046* (2013.01); *A61L 2209/132* (2013.01)

(58) Field of Classification Search
CPC ................. B01F 3/04; B01F 3/06; A61L 9/12
USPC ........... 261/76, 81, 94, 95, DIG. 88; 422/124; 239/54, 60
See application file for complete search history.

(56) References Cited

U.S. PATENT DOCUMENTS

| 5,565,148 A | 10/1996 | Pendergrass, Jr. ............... 261/30 |
| 6,712,287 B1 | 3/2004 | Le Pesant et al. ............... 239/67 |

(Continued)

FOREIGN PATENT DOCUMENTS

| CN | 1666573 | 9/2005 | ................ A61L 9/03 |
| CN | 1781133 | 5/2006 | .............. G09F 15/00 |

(Continued)

OTHER PUBLICATIONS

International Search Report (in Japanese), dated Sep. 4, 2012, and the Written Opinion of the International Searching Authority (in Japanese), dated Sep. 4, 2012, issued in Applicant's corresponding PCT Application No. PCT/JP2012/069193 filed on Jul. 27, 2012.

(Continued)

*Primary Examiner* — Robert A Hopkins
(74) *Attorney, Agent, or Firm* — Gerald T. Bodner

(57) ABSTRACT

[Structure] An olfactory display 10 includes a housing 12 having an emitting port 22, and presents a fragrance within a range bounded in terms of time and space. Within the housing 12, a fragrance chamber 14 having an air inlet 26 and a fragrance outlet 24 which is communicated with the emitting port 22 is formed, and in the fragrance chamber 14, a solid-like fragrance source 20 is accommodated. Furthermore, in the fragrance chamber 14, there is provided with a airflow source 16 comprising a diaphragm 34 having a piezoelectric device 32. In presenting a fragrance, an air is sent into the fragrance chamber 14 from the air inlet 26 by the airflow source 16, and accordingly, the air within the fragrance chamber 14, which including a gas-like fragrance component volatilized from the fragrance source 20 is emitted from the emitting port 22 passing through the fragrance outlet 24.

12 Claims, 10 Drawing Sheets

(56) References Cited

U.S. PATENT DOCUMENTS

| | | | |
|---|---|---|---|
| 7,300,624 B2 * | 11/2007 | Crosby | A61K 36/16 422/124 |
| 7,363,737 B2 | 4/2008 | Benalikhoudja | 40/407 |
| 7,687,744 B2 | 3/2010 | Walter et al. | 219/505 |
| 2005/0089415 A1 | 4/2005 | Cho et al. | 417/413.2 |
| 2009/0108094 A1 * | 4/2009 | Ivri | A61L 9/14 239/101 |
| 2011/0200488 A1 | 8/2011 | Cennini et al. | 422/105 |

FOREIGN PATENT DOCUMENTS

| | | | |
|---|---|---|---|
| CN | 1892028 | 1/2007 | F04B 43/02 |
| CN | 201010407 | 1/2008 | B66B 11/02 |
| CN | 101121037 | 2/2008 | A61L 9/03 |
| CN | 102196824 | 9/2011 | A61L 9/03 |
| CN | 102338072 | 2/2012 | F04B 45/047 |
| JP | 10-146385 | 6/1998 | A61L 9/12 |
| JP | 2003-260122 | 9/2003 | A61L 9/12 |
| JP | 2004-121594 | 4/2004 | A61L 9/12 |
| JP | 2005-095310 | 4/2005 | A61L 9/14 |
| JP | 2008-257216 | 10/2008 | G09F 19/00 |
| JP | 2008-264308 | 11/2008 | A61L 9/16 |
| JP | 2010-039333 | 2/2010 | G09F 19/00 |
| JP | 2010-274183 | 12/2010 | B01D 53/26 |
| JP | 2011-081035 | 4/2011 | G09F 19/00 |
| JP | 3174255 | 2/2012 | A61L 9/12 |

OTHER PUBLICATIONS

Communication Pursuant to Rule 164(1) EPC, dated Dec. 1, 2015, issued by the European Patent Office in Applicants' corresponding European Patent Application No. 12868332.3, filed on Jul. 27, 2012, enclosing a Supplementary Partial European Search Report and Annex to the European Search Report, dated Nov. 20, 2015, issued by the European Patent Office in Applicants' corresponding European Patent Application No. 12868332.3, filed on Jul. 27, 2012.

Communication Pursuant to Rule 62 EPC, in English, dated Feb. 5, 2016, issued by the European Patent Office in Applicants' corresponding European Patent Application No. 12868332.3, filed on Jul. 27, 2012, enclosing an extended European Search Report which includes the Supplementary European Search Report, the European Search Opinion and Annex to the European Search Report, in English, dated Jan. 26, 2016, issued by the European Patent Office in Applicants' corresponding European Patent Application No. 12868332.3, filed on Jul. 27, 2012.

* cited by examiner

OLFACTORY DISPLAY

TECHNICAL FIELD

The present invention relates to an olfactory display, and more specifically, an olfactory display which presents a fragrance within a range bounded in terms of time and space.

BACKGROUND ART

Recently, there are proposed various kinds of olfactory displays which present a fragrance (olfactory information) in cooperation with an audio-visual display of a television, a personal computer, etc. for a purpose of information presentation by which a high presence, a high immersion feeling and so on can be applied to a user. Here, in a case where a specific fragrance is to be presented for a certain degree of a long period of time, it is sufficient to simply diffuse a fragrance in a space. However, in order to present a fragrance in synchronization with a scene change of a content displayed by an audio-visual display, for example, a temporal control (temporal locality) of fragrance presentation becomes needed. Furthermore, in order to present a fragrance to only a target person, for example, a spatial control (spatial locality) of fragrance presentation becomes needed. Furthermore, if the temporal locality and the spatial locality for the fragrance presentation are implemented, not only an aromatic material to be used can be greatly saved but also a problem of a lingering fragrance can be solved. From these, an olfactory display which presents a fragrance controllable in terms of time and space, that is, an olfactory display which can present a fragrance within a range bounded in terms of time and space is expected.

The patent literature 1 discloses an example of a conventional olfactory display. The olfactory display (aroma generating apparatus) of the patent literature 1 comprises an aromatic material accommodating portion which accommodates a solid-like aromatic material, and pumps are provided at an inlet side and an outlet side of the aromatic material accommodating portion, respectively. In generating the fragrance, the inlet side pump is rotated to send an air into the aromatic material accommodating portion, whereby an air (fragrance) to which the aroma is added can be pushed out of the aromatic material accommodating portion, and at the same time, by rotating the outlet side pump, the fragrance is discharged to an external from the fragrance discharging port.

Furthermore, another example of a conventional olfactory display is disclosed in the patent literature 2. The olfactory display (a controlled-type aroma outputting apparatus) of the patent literature 2 comprises an aromatic material accommodating portion which accommodates a liquid aromatic material and an aromatic material emitter of an ink-jet type using a piezoelectric device. In generating the fragrance, the aromatic material is injected into an internal of the apparatus as a liquid particle by the aromatic material emitter, and the aromatic material volatilized after the injection is discharged to an external of the apparatus by a blower fan.

Patent Literature 1: Japanese Patent Application Laying-Open No. 2004-121594 [A61L9/12]

Patent Literature 2: Japanese Patent Application Laying-Open No. H10-146385 [A61L9/12]

SUMMARY OF THE INVENTION

Problem to be Solved by the Invention

In the art of the patent literature 1, the fragrance is merely pushed-out to the external from the aromatic material accommodating portion by the rotation of a rotor of the pump, that is, the fragrance is merely diffused to a surrounding space, and therefore, the spatial control of the fragrance presentation is not considered. That is, the presentation of the fragrance within a range bounded in terms of space is not implemented. Furthermore, since structure is complex, there is a limit for a miniaturization.

Furthermore, in the art of the patent literature 2, the aromatic material is discharged to the external by using two mechanisms of the aromatic material emitter and the blower fan, and therefore, the apparatus becomes large. Furthermore, since the blowing (generation of wind pressure) by the blower fan is dependent on a rotation speed of the fan, a quick temporal control cannot be performed, and thus, a time lag possibly occurs. In addition, in the patent literature 2, there is an example of a manner that the aromatic material is directly emitted to the external of the apparatus by the aromatic material emitter of the ink-jet type; however, if the aromatic material is directly emitted as the liquid particle, there occurs a problem of a remaining fragrance due to adhesion of the aromatic material. Therefore, a deodorizing means is indispensable, and as a result thereof, the apparatus becomes large.

Therefore, it is a primary object of the present invention to provide a novel olfactory display.

It is another object of the present invention to provide an olfactory display capable of presenting a fragrance within a range bounded in terms of time and space and that an apparatus itself can be miniaturized.

It is a further object of the present invention to provide an olfactory display capable of presenting two or more kinds of fragrances by a single apparatus.

Means for Solving the Problem

The present invention employs following features in order to solve the above-described problems. It should be noted that reference numerals and the supplements inside the parentheses show one example of a corresponding relationship with the embodiments described later for easy understanding of the present invention, and do not limit the present invention.

A first invention is an olfactory display presenting a fragrance within a range bounded in terms of time and space, comprising: a housing having an emitting port; a fragrance chamber formed in the housing and having an air inlet and a fragrance outlet which is communicated with the emitting port; a solid-like fragrance source accommodated in the fragrance chamber; and an airflow source which sends an air from the air inlet into the fragrance chamber by using a diaphragm having a piezoelectric device.

In the first invention, the olfactory display (10) includes the housing (12) having the emitting port (22) and the airflow source (16), and presents a fragrance (or smell or scent) within a range bounded in terms of time and space in cooperation with an audio-visual display of a personal computer, a television, etc., for example. Within the housing, the fragrance chamber (14) provided with the air inlet (26) and the fragrance outlet (24) which is communicated with the emitting port is formed, and within the fragrance chamber, the solid-like fragrance source (20) is accommodated. As the solid-like fragrance source, an object that a liquid aromatic material is soaked in a granular porous material is used, for example. The airflow source comprises the diaphragm (34) onto which the piezoelectric device (32) is adhered, and if and when an alternating voltage is applied to the piezoelectric device, the piezoelectric device vibrates the diaphragm to generate an air flow. In presenting a fragrance by the olfactory display, an air is sent into the fragrance chamber from the air inlet by the airflow source, and the air within the fragrance chamber, which including a gas-like fragrance component volatilized from the fragrance source is emitted from the emitting port passing through the fragrance outlet.

In accordance with the first invention, since the airflow source utilizing the diaphragm having the piezoelectric device is used, it is possible to produce a high static pressure within the fragrance chamber with a short period of time, whereby it becomes possible to present a fragrance within a range extremely bounded in terms of space with an excellent responsiveness. That is, since a time-space-control by a single mechanism (the airflow source) becomes possible, the olfactory display can be miniaturized.

A second invention is according to the first invention, wherein the fragrance outlet is formed in a direction intersecting orthogonally to the air inlet.

In the second invention, the fragrance outlet (24) is formed in a direction intersecting orthogonally to the air inlet (26), whereby a moderate turbulent flow occurs in the air flow within the fragrance chamber (14) in presenting a fragrance.

In accordance with the second invention, since the turbulent flow occurs in the air flow within the fragrance chamber, it is possible to use a whole fragrance source within the fragrance chamber in a good balance.

A third invention is according to the first or second invention, further comprising an operation noise suppressing portion provided at a side of an upper stream of the airflow source.

In the third invention, at an upper side of the air flow by the airflow source (16), the operation noise suppressing portion (18) is provided. The operation noise suppressing portion is formed with a cavity portion at the upper stream side of the diaphragm (34) of the airflow source, and the cavity portion is partitioned with a partitioning wall (48), for example, whereby a leakage of the operation noise from an outside air port (46a) can be suppressed.

In accordance with the third invention, it is possible to naturally convey a fragrance to the user without giving an uncomfortable feeling due to the operation noise to the user.

A fourth invention is according to any one of the first to third inventions, further comprising: a plurality of fragrance chambers formed by partitioning an internal space of the housing by partitioning walls; and a plurality of fragrance paths extending toward the emitting port from respective fragrance outlets formed in the plurality of fragrance chambers, wherein the fragrance source is accommodated in at least one of the plurality of fragrance chambers, and the airflow source is provided in each of the plurality of fragrance chambers, and the plurality of fragrance paths are joined to each other at a position near the emitting port to form a single common path.

In the fourth invention, the plurality of fragrance chambers (14) partitioned with the partitioning walls (50) are formed in the housing (12), and the solid-like fragrance source (20) is accommodated in at least one of the plurality of the fragrance chambers. Furthermore, in each of the fragrance chambers, an individual airflow source (16) is provided. Respective fragrance outlets (24) formed in the respective fragrance chambers are communicated with the emitting port (22) via the fragrance paths (52). The respective fragrance paths extend toward the emitting port from the respective fragrance outlets, and joined to each other at the position near the emitting port to be rendered as the single common path (54) reaching the emitting port.

In accordance with the fourth invention, since the plurality of independent fragrance chambers are provided in the housing, if the fragrance sources having different fragrances are accommodated in the respective fragrance chambers, it becomes possible to present a plurality of kinds of fragrances. Furthermore, since the common path that the respective fragrance paths are joined to each other is formed at the position near the emitting port, and the fragrance is emitted from the single emitting port, not only it becomes possible to present a mixed fragrance but also adjustment for the spatial control becomes easy.

A fifth invention is according to the fourth invention, further comprising venturi tube structure in a portion that the plurality of fragrance paths are joined to each other.

In accordance with the fifth invention, in a joining portion (56) of the fragrance paths (52), the venturi tube structure is provided. In addition, the venturi tube structure means structure utilizing a venturi effect that by narrowing a fluid flow, a flowing speed is increased, and thus, a low pressure is produced.

In accordance with the fifth invention, since the venturi tube structure is formed at the joining portion of the fragrance paths, a velocity of the fragrance passing the joining portion is sufficiently accelerated, and therefore, not only adhesion of the fragrance component at the joining portion is prevented but also the fragrance is emitted from the emitting port with a higher directivity.

A sixth invention is an olfactory display which presents a fragrance within a range bounded in terms of time and space, comprising: a housing having an emitting port; a plurality of fragrance chambers formed by partitioning an internal space of the housing with the partitioning walls, each fragrance chamber having an air inlet and a fragrance outlet; a solid-like fragrance source accommodated in at least one of the fragrance chambers; a plurality of airflow sources each of which is provided in each of the fragrance chambers and sends an air from the air inlet into the fragrance chamber by using a diaphragm provided with a piezoelectric device; and a plurality of fragrance paths each extending from the fragrance outlets toward the emitting port, wherein the plurality of fragrance paths are joined to each other in a position near the emitting port to form a single common path and venturi tube structure is formed at the joining portion.

In the sixth invention, the olfactory display (10) includes the housing (12) having the emitting port (22), and presents a fragrance within a range bounded in terms of time and space in cooperation with an audio-visual display of a personal computer, a television, etc., for example. In the housing, the plurality of fragrance chambers (14) partitioned by the partitioning walls (50) are formed, and within at least one of the fragrance chambers, the solid-like fragrance source (20) is accommodated. As the solid-like fragrance source, an object that a liquid aromatic material is soaked in a granular porous material is used, for example. Furthermore, in each fragrance chamber, an individual airflow source (16) is provided. The airflow source comprises the diaphragm (34) onto which the piezoelectric device (32) is adhered, and if and when an alternating voltage is applied to the piezoelectric device, the piezoelectric device vibrates the diaphragm to generate an air flow. Respective fragrance outlets (24) formed in the respective fragrance chambers are communicated with the emitting port (22) via the fragrance paths (52). The respective fragrance paths extend toward the emitting port from the respective fragrance outlets, and joined to each other at the position near the emitting port to be rendered as the single common path (54), and in a joining portion (56) of the fragrance paths (52), the venturi tube structure is provided. In addition, the venturi tube structure means structure utilizing a venturi effect that by narrowing a fluid flow, a flowing speed is increased, and thus, a low pressure is produced.

In presenting a fragrance by such an olfactory display, an air is sent into the fragrance chamber from the air inlet (26) by the airflow source, and the air within the fragrance chamber, which including a gas-like fragrance component volatilized from the fragrance source is emitted from the emitting port passing through the fragrance outlet and the fragrance path. At this time, since the venturi tube structure is formed at the joining portion of the fragrance paths, a velocity of the fragrance passing the joining portion can be sufficiently increased.

In accordance with the sixth invention, since the airflow source utilizing the diaphragm having the piezoelectric device is used, it is possible to produce a high static pressure within the fragrance chamber with a short period of time, whereby it becomes possible to present a fragrance within a range extremely bounded in terms of space with an excellent responsiveness. That is, since a time-space-control by a single mechanism (the airflow source) becomes possible, the olfactory display can be miniaturized.

Furthermore, if the fragrance sources having different fragrances are accommodated in the respective fragrance chambers, it becomes possible to present a plurality of kinds of fragrances. At this time, since the venturi tube structure is formed at the joining portion of the fragrance paths, a velocity of the fragrance passing the joining portion is sufficiently accelerated, and therefore, not only adhesion of the fragrance component at the joining portion is prevented but also the fragrance is emitted from the emitting port with a higher directivity. Furthermore, since the common path that the respective fragrance paths are joined to each other is formed at the position near the emitting port, and the fragrance is emitted from the single emitting port, not only it becomes possible to present a mixed fragrance but also adjustment for the spatial control becomes easy.

A seventh invention is according to any one of the fourth to sixth inventions, wherein the fragrance path is formed by a penetrating hole passing through an internal of the partitioning wall.

In the seventh invention, the fragrance path (52) is formed by the penetrating hole passing through the partitioning wall (50) which partitions the internal of the housing (12), whereby the olfactory display (10) can be miniaturized in comparison with a case where a space for forming the fragrance path is separately provided.

An eighth invention is according to any one of the fifth to seventh inventions, wherein the venturi tube structure includes a diameter-reduced portion formed by reducing a diameter of the common path toward a side of the emitting port.

In the eighth invention, in the common path (54), the diameter-reduced portion (60) that the diameter of the common path is gradually reduced toward the emitting port (22) is formed, and the diameter-reduced portion shows the venturi effect.

A ninth invention is according to any one of the fifth to eighth inventions, wherein the venturi tube structure includes a partitioning plate provided at the joining portion of the plurality of fragrance paths.

In the ninth invention, at the joining portion (56) of the fragrance paths (52), the partitioning plate (58) which partitions between the fragrance paths is formed, and the partitioning plate shows the venturi effects. The partitioning plate is formed as a flat plane a tip end of which is pointed toward a side of the emitting port (22), for example, and also functions as a guide plate which guides the fragrance flowing into each of the fragrance paths in a direction of the emitting port.

A tenth invention is according to any one of the fourth to ninth inventions, wherein at least one of the fragrance chambers is accommodated with a granular body into which no fragrance component is soaked as the fragrance source.

In the tenth invention, at least one of the fragrance chambers (14) is not accommodated with the fragrance source (20) and accommodated with only the granular body such as a porous material or non-porous material to which no liquid aromatic material is soaked. For example, after a fragrance is presented, by emitting an odorless air by operating the airflow source (16) of the fragrance chamber in which no fragrance source is accommodated, a quicker deodorization becomes possible. Furthermore, if the airflow source of the fragrance chamber accommodating the fragrance source and the airflow source of the fragrance chamber not accommodating the fragrance source are simultaneously or in a time-shared manner operated, it is possible to adjust a density of an emitting fragrance component.

In accordance with the tenth invention, a quicker deodorization becomes possible and density adjustment of the fragrance component also becomes possible.

An eleventh invention is according to any one of the fourth to tenth inventions, wherein at least one of the fragrance chambers is rendered as an empty chamber.

In the eleventh invention, at least one of the fragrance chambers (14) is not accommodated with fragrance source (20) to be rendered as the empty chamber. For example, after a fragrance is presented, by emitting an odorless air by operating the airflow source (16) of the fragrance chamber which is rendered as the empty chamber, a quicker deodorization becomes possible. Furthermore, if the airflow source of the fragrance chamber accommodating the fragrance source and the airflow source of the fragrance chamber which is rendered as the empty chamber are simultaneously or in a time-shared manner operated, it is possible to adjust a density of an emitting fragrance component.

In accordance with the eleventh invention, a quicker deodorization becomes possible and density adjustment of the fragrance component also becomes possible.

A twelfth invention is according to any one of the fourth to eleventh inventions, further comprising an auxiliary airflow source provided with a diaphragm having a piezoelectric device; and an auxiliary path which communicates the auxiliary airflow source and the common path.

In the twelfth invention, the olfactory display further comprises the auxiliary airflow source (62) provided independently from the fragrance chambers and separately from the airflow sources (16) provided in the fragrance chambers (14). As the auxiliary airflow source, a mechanism similar to the airflow source, i.e., an object that is provided with a diaphragm to which the piezoelectric device is adhered and the diaphragm is vibrated to generate an air flow if and when an alternating voltage is applied to the piezoelectric device is used. Furthermore, in the housing (12), the auxiliary path (64) which communicates the auxiliary airflow source and the common path (54) is provided.

In presenting a fragrance to the user by such an olfactory display (10), the airflow source provided in the fragrance chamber which accommodates a target fragrance source (20) is operated, and at the same time or in a time-shared manner, the auxiliary airflow source is operated. Then, the fragrance toward the emitting port (22) passing through the fragrance path (52) is joined with an odorless air discharged from the auxiliary airflow source in the common path to be accelerated and thus vigorously emitted from the emitting port with straightness.

In accordance with the twelfth invention, since the auxiliary airflow source is provided, the presentation of a fragrance with better directivity becomes possible. Furthermore, since stagnation of the fragrance in the common path is further suppressed, adhesion of the fragrance component to the common path can be more effectively prevented.

A thirteenth invention is according to the twelfth invention, wherein a discharging performance of the auxiliary airflow source is rendered higher than a discharging performance of the airflow source.

In the thirteenth invention, by making a diameter of the piezoelectric device provided on the auxiliary airflow source (62) larger than a diameter of the piezoelectric device (32) provided on the airflow source (16), the discharging performance of the auxiliary airflow source, that is, its performance for sending off an air is made higher than that of the airflow source. Accordingly, it is possible to extend a distance of the presentation of a fragrance. Furthermore, since it is possible to vigorously emit the odorless air, it is possible to show a higher deodorization effect.

Advantages of the Invention

In accordance with the present invention, by using a airflow source utilizing a diaphragm having the piezoelectric device, a time-space-control by a single mechanism becomes possible, and accordingly, an olfactory display can be miniaturized.

In accordance with one of the fourth to sixth inventions, since a plurality of independent fragrance chambers are provided in a housing, if fragrance sources having different fragrances are accommodated in the respective fragrance chambers, it becomes possible to present a plurality of kinds of fragrances. Furthermore, since a common path that respective fragrance paths are joined to each other is formed at the position near an emitting port, and the fragrance is emitted from the single emitting port, not only it becomes possible to present a mixed fragrance but also adjustment for the spatial control becomes easy. Furthermore, if venturi tube structure is formed at the joining portion of the fragrance paths, a velocity of the fragrance passing the joining portion is sufficiently accelerated, and therefore, not only adhesion of the fragrance component at the joining portion is prevented but also the fragrance can be emitted from the emitting port with a higher directivity.

The above described objects and other objects, features, aspects and advantages of the present invention will become more apparent from the following detailed description of the present invention when taken in conjunction with the accompanying drawings.

FORMS FOR EMBODYING THE INVENTION

Figure 1:
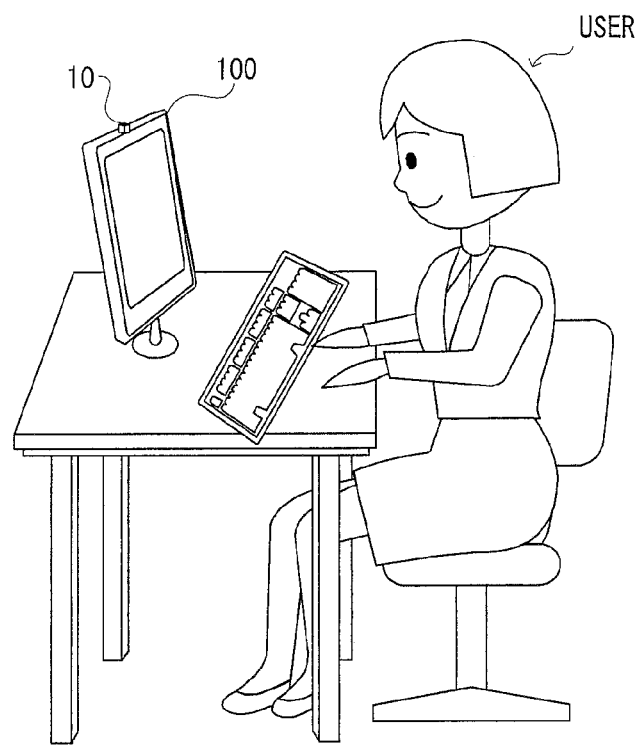
FIG. 1 is a view showing a manner that a fragrance is presented to a user by utilizing an olfactory display which is an embodiment according to the present invention.

With referring to FIG. 1, an olfactory display 10 which is an embodiment according to the present invention is used for enhancing a reality and a presence of a content by presenting to a user the content including an image and sound to which a fragrance (olfactory information) is added. The olfactory display 10 presents a fragrance in a time-space-controllable manner, that is, within a range bounded in terms of time and space in cooperation with various kinds of audio-visual displays such as a personal computer, a television, a radio, a game machine, a DVD player, a video deck, a mobile phone, etc., for example.

FIG. 1 shows a manner that the olfactory display 10 is used in cooperation with a personal computer as an example. In such a case, the olfactory display 10 is attached to an LCD display 100, a keyboard or the like such that an emitting port 22 (see FIG. 2) for emitting a fragrance is turned to a direction of a face of the user.

Figure 2:
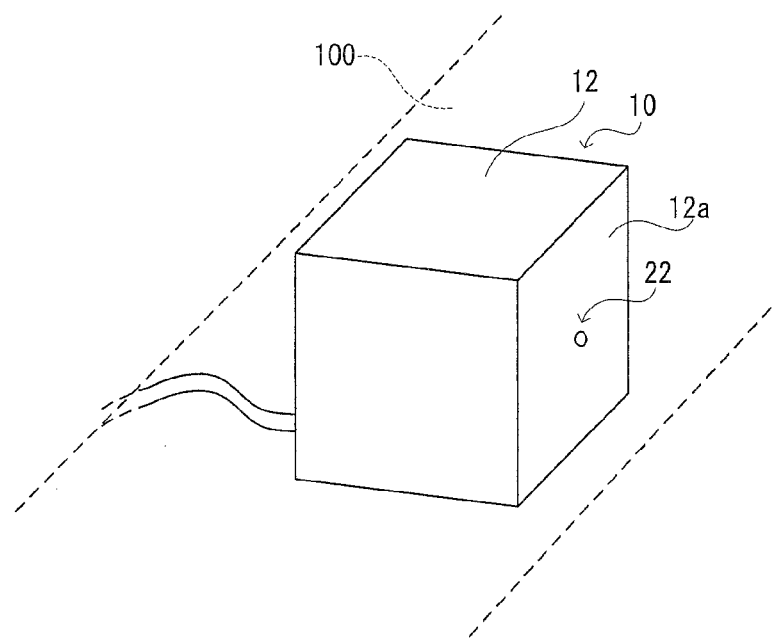
FIG. 2 is a perspective view showing an appearance of the olfactory display in FIG. 1.
Figure 3:
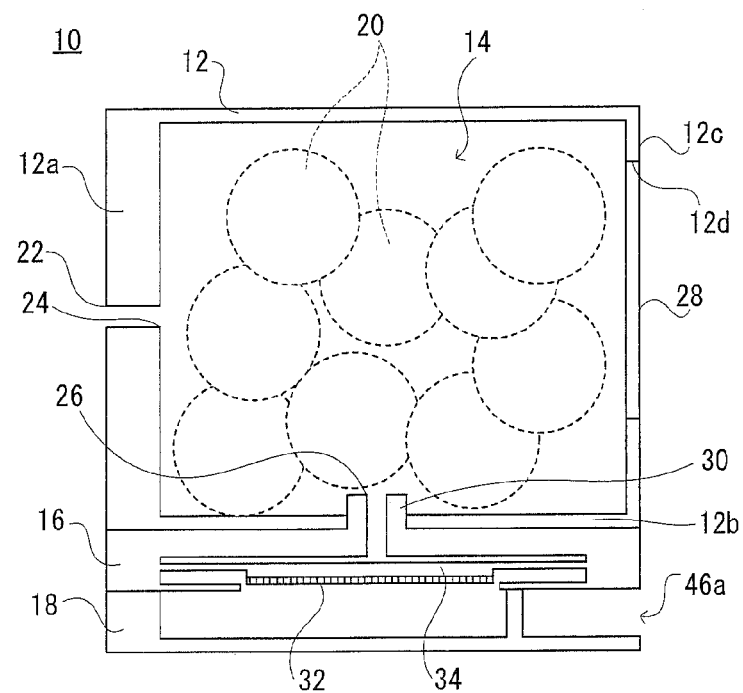
FIG. 3 is a cross-sectional view showing internal structure of the olfactory display in FIG. 1 in viewing from a side surface direction.

As shown in FIG. 2 and FIG. 3, the olfactory display 10 is a ultrasmall olfactory display which is formed in a shape of a cube approximately 20 mm on each side, and has a housing 12, a fragrance chamber 14, a airflow source 16 and an operation noise suppressing portion 18.

The housing 12 is formed in a shape of a rectangular parallelepiped by a suitable material such as an acrylic resin, a fluororesin, a stainless steel, etc. An internal space of the housing 12 is used as the fragrance chamber 14, and within the housing 12, that is, within the fragrance chamber 14, a solid-like fragrance source 20 is accommodated.

The emitting port 22 is formed in a center portion of a side wall 12a at a front side (a user side) of the housing 12. The emitting port 22 is communicated with a fragrance outlet 24 of the fragrance chamber 14 via a communication hole extending in a thickness direction of the side wall 12a. Furthermore, a nozzle 30 of the airflow source 16 is connected to a center portion of a bottom wall 12b of the housing 12 so as to be penetrated. The nozzle 30 functions as an air inlet 26 for making an air flow into the fragrance chamber 14. Furthermore, an opening 12d for taking a fragrance source 20 in or out of the fragrance chamber 14 is formed on a side wall 12c at a rear side of the housing 12; however, the opening 12d is properly sealed with using a sponge stopper 28 made of polyurethane, silicone or the like, after the fragrance source 20 is accommodated. That is, the fragrance chamber 14 is a sealed space having the air inlet 26 and the fragrance outlet 24 which is formed in a direction intersecting orthogonally to the air inlet 26.

A diameter of the air inlet 26 (an inner diameter of the nozzle 30) is 0.8 mm, for example. Furthermore, diameters of the emitting port 22 and the fragrance outlet 24 are respectively 0.8 mm, for example, and a length of the communicating hole connecting the emitting port 22 and the fragrance outlet 24, i.e. a thickness of the side wall 12a is 2.0 mm, for example. In addition, since the diameters of the emitting port 22, the fragrance outlet 24 and the air inlet 26 are thus small, a leakage of a fragrance from the fragrance chamber 14 almost does not occur at a time that the airflow source 16 is not operated. Furthermore, in this embodiment, in order to render the length of the communicating hole connecting the emitting port 22 and the fragrance outlet 24 2.0 mm, an entire thickness of the side wall 12a is also rendered as 2.0 mm; however, only a portion of the emitting port 22 may be formed to be projected in a nozzle shape. Furthermore, it is possible to diameter-reduce the communicating hole connecting the emitting port 22 and the fragrance outlet 24 toward a side of the emitting port 22. In addition, sizes of the emitting port 22, fragrance outlet 24 and air inlet 26, the length of the communicating hole connecting the emitting port 22 and the fragrance outlet 24 and so on are properly changeable according to a size of the fragrance chamber 14 and the performance of the airflow source 16 or the directivity and the distance found to a fragrance being emitted.

The solid-like fragrance source 20 is manufactured by soaking a liquid aromatic material into a granular porous material (impregnation) and holding the aromatic material on an outer surface and within pores of the porous material. For the aromatic material, natural aromatic materials, synthetic aromatic materials and compound aromatic materials thereof are available appropriately. For the porous material, a granular body such as calcium silicate, silica gel, rock wool, diatomaceous earth, zeolite, peat, charcoal, vermiculite, bentonite, perlite, carbon nanotube, active carbons, etc. are available appropriately. A particle size and shape of the porous material is not restricted especially, but, if a passage resistance, etc. within the fragrance chamber 14 are taken into account, it is preferable that the particle size is around 1-6 mm and the shape is a globoid. In this embodiment, the fragrance source 20 is formed by using sixteen particles prepared in a manner where the liquid aromatic material is soaked into the globoid of the calcium silicate having an average particle size of 4 mm.

Below the fragrance chamber 14, the airflow source 16 is provided such that the nozzle 30 of the airflow source 16 is communicated with the internal of the fragrance chamber 14.

Figure 4:
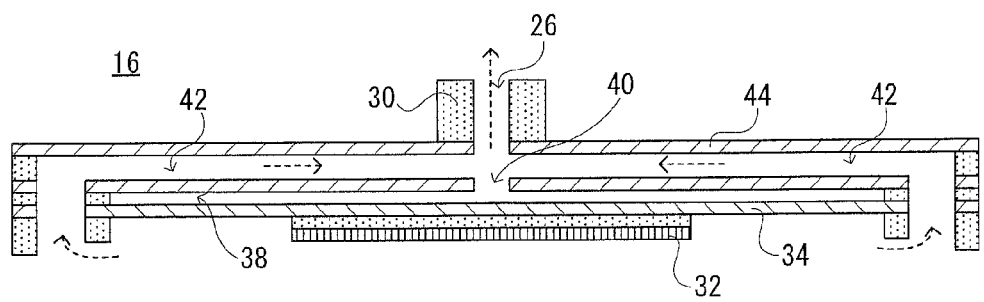
FIG. 4 is a cross-sectional view showing an enlarged cross-section at a time that an airflow source provided on the olfactory display in FIG. 1 is cut in a diagonal line direction.

FIG. 4 shows an enlarged cross-section in a state that the airflow source 16 is cut in a direction of a diagonal line. The airflow source 16 is a piezoelectric type, being provided with a diaphragm 34 onto which a piezoelectric device (piezoelectric element) 32 is adhered, and by applying an alternating voltage (sign wave voltage or rectangular wave voltage) to the piezoelectric device 32, the diaphragm 34 is bent and vibrated in a thickness direction thereof to generate an air flow.

In the following, an operation of the airflow source 16 will be briefly described. In the airflow source 16, in response to the vibration of approximately 26 kHz of the diaphragm 34 adhered with a disc-like piezoelectric device 32, a suction and discharge of the air to and from an air hole 40 formed in a pump room 38 are repeated. The air taken into the pump room 38 from a suction passage 42 at a time of suction passes at a time of discharge through the nozzle 30 which is arranged coaxially with the air hole 44 and provided on a top plate 44, and expanded in a tapered conduit in the nozzle 30 to be discharged. At this time, since a negative pressure portion occurs in a space between the air hole 40 and the nozzle 30 due to a venturi effect, the air in the suction passage 42 is continuously sucked, whereby a continuous pump operation toward the nozzle 30 from the suction passage 42 can be obtained.

The airflow source (airflow source of the piezoelectric system) 16 thus driven by the piezoelectric device 32 does not have a rotation mechanism such as a blower fan or a scroll blower, and thus, can be reduced in a size and a height, and further a consumption electricity is also small. In addition, such the airflow source is of no vibration essentially and has a feature that a higher static pressure can be produced within a short time period. For such a airflow source 16, a micro blower (type number: MZBX001) manufactured by Murata Manufacturing Co., Ltd, for example, is available.

Figure 5:
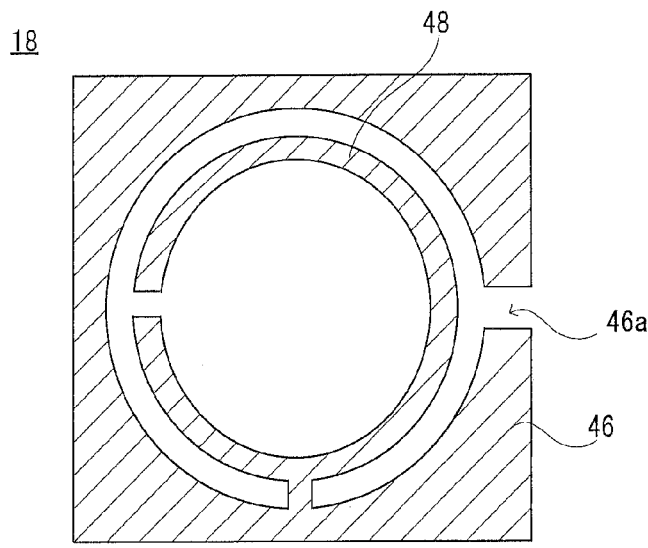
FIG. 5 is a cross-sectional view showing a cross-section at a time that an operation noise suppressing portion provided on the olfactory display in FIG. 1 is cut in a horizontal direction.

Returning to FIG. 3, below the airflow source 16 (an upstream side of the air passage), the operation noise suppressing portion 18 for suppressing a leakage of an operation noise of the airflow source 16 (a vibration noise of the diaphragm 34) to the external is provided. The operation noise suppressing portion 18 is made of a suitable material such as an acrylic resin, a fluororesin, a stainless steel, etc., and formed with a cavity portion below the diaphragm 34. FIG. 5 shows a cross-section in a state that the operation noise suppressing portion 18 is cut in a horizontal direction. As shown in FIG. 5, an air port 46a for sucking-in an air at a time that the airflow source 16 is operated is formed on a side wall 46 of the operation noise suppressing portion 18, and the internal of the operation noise suppressing portion 18 is partitioned by a C-letter shaped partitioning wall 48. Therefore, since the operation noise of the airflow source 16 reaches the air port 46a with making a detour through a maze-like air passage, a leakage of the operation noise from the air port 46a can be suppressed. By providing such an operation noise suppressing portion 18, it is possible to naturally convey a fragrance to the user without giving to the user an uncomfortable feeling due to the operation noise. It is to be noted that the internal structure of the operation noise suppressing portion 18 is not restricted to a manner shown in FIG. 5. For example, the operation noise suppressing portion 18 may be a mere cavity with no partitioning wall 48 or may be provided with a partitioning wall having another shape.

As described above, the olfactory display 10 having such the structure presents to the user a content which is presented by a personal computer or the like and includes an image and sound by adding a fragrance to the content. A controller (not shown) of the olfactory display 10 applies an alternating voltage to the piezoelectric device 32 of the airflow source 16 in response to an instructing signal sent from the personal computer or the like. If the diaphragm 34 is bent and vibrated due to the application of the alternating voltage, an air is sucked from the air port 46a of the operation noise suppressing portion 18, and a high speed and high pressure air is sent into the fragrance chamber 14 from the nozzle 30 of the airflow source 16, that is, from the air inlet 26. A gas-like fragrance component volatilized from the fragrance source 20 is included in the air within the fragrance chamber 14, and the air including such a fragrance component is emitted from the emitting port 22 passing through the fragrance outlet 24. Then, when the application of the alternating voltage to the piezoelectric device 32 is stopped, the emission of the air including the fragrance component from the emitting port 22 is also stopped. At this time, since the piezoelectric type airflow source 16 is utilized, the start and stop of the emission of the air including the fragrance component is performed with excellent responsiveness (that is, a precise temporal control is possible), and further, the presentation of a continuous and constant fragrance not being pulsative is also possible. Furthermore, since the fragrance outlet 24 is formed in a direction intersecting orthogonally to the air inlet 26, a modulate turbulent flow occurs in the flow of air within the fragrance chamber 14, and therefore, the fragrance source 20 in the fragrance chamber 14 can be entirely used with a good balance.

Figure 6:
FIG. 6 is a view showing a spatial spread of a fragrance component emitted from the olfactory display in FIG. 1.

FIG. 6 is a view schematically showing a spatial spread of a fragrance emitted from the olfactory display 10. If and when the alternating voltage of a frequency of 26 kHz and a magnitude of 19.5 Vp-p is applied to the piezoelectric device 32 to operate the olfactory display 10 practically, it is confirmed that a wind velocity of the air including the fragrance component and being emitted from the emitting port 22 is approximately 200 mm/second. Furthermore, it is also confirmed that the spatial spread $\phi$ (phi) of the fragrance component stays within 50 mm at a point that a distance L from the emitting port 22 is 300 mm. Thus, the olfactory display 10 can present a fragrance within a range extremely bounded in terms of space, that is, only in a vicinity of a face of the user. Furthermore, since it is possible to present a fragrance within a range extremely bounded in terms of space, not only the aromatic material to be used can be greatly saved but also a lingering fragrance hardly occurs. If and when a fragrance is emitted from the olfactory display 10 for three (3) seconds to present a fragrance to the user, after stopping the presentation of the fragrance, the fragrance component is diffused and diluted in around a few seconds, and a surrounding space becomes odorless with using no deodorization device. Furthermore, even if the emission of the fragrance for three (3) seconds is repeated more than a thousand (1000) times, no change occurs in a strength of a fragrance to be presented. In addition, a gas-like fragrance component volatilized from the fragrance source 20 fills in the fragrance chamber 14 with an interval of 10-30 seconds after the presentation of the fragrance for three (3) seconds.

Figure 7:
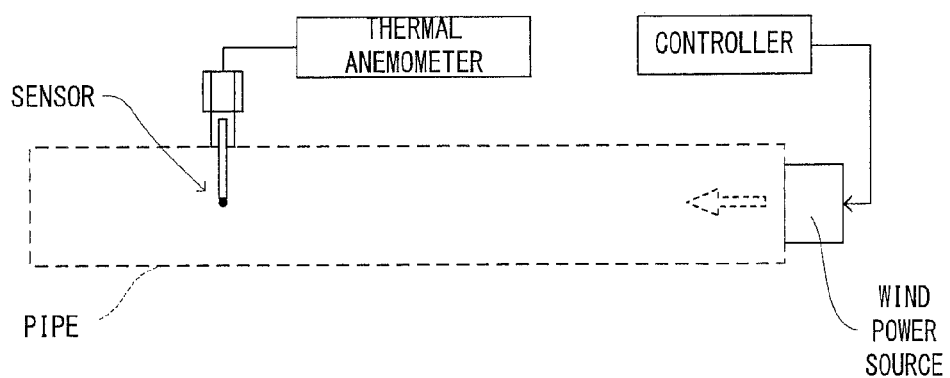
FIG. 7 is a view showing structure of an evaluation system utilized for evaluation of a performance of the airflow source of FIG. 4.
Figure 8:
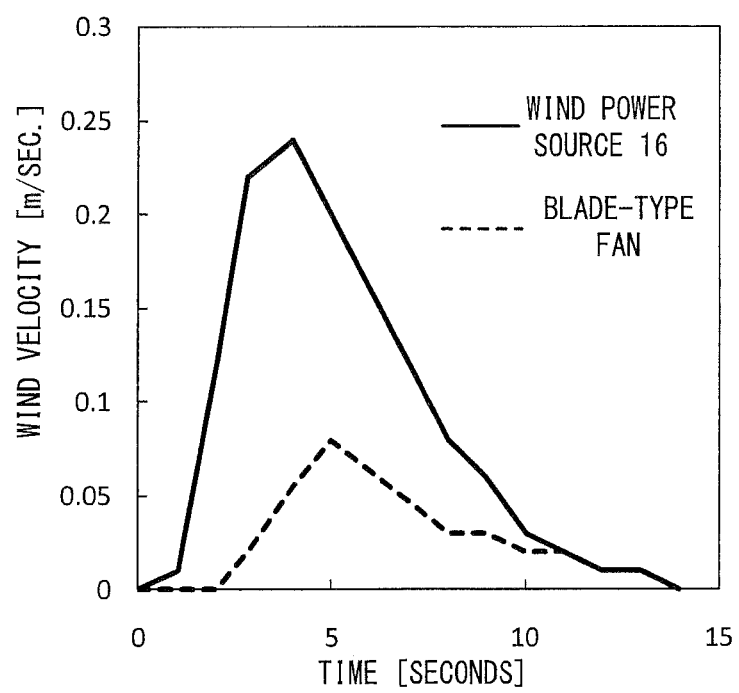
FIG. 8 is a graph showing a result of the performance evaluation of the airflow source of FIG. 4.

In addition, because a function capable of producing a high static pressure within a short period of time in the fragrance chamber 14 is needed as a function of the airflow source 16, an experimentation comparing a static pressure producing speed by the airflow source 16 which is used in this embodiment and a static pressure producing speed by a conventional blade-type fan with each other has been performed. FIG. 7 shows structure an evaluation system utilized for evaluation of a performance of the airflow source 16, and FIG. 8 shows a result of the performance evaluation.

As shown in FIG. 7, a thermal anemometer is utilized for measurement of the static pressure (wind velocity). A sensor of the thermal anemometer is set in a PVC pipe of a length of 420 mm and an inner diameter of 53 mm $\phi$ for not being influenced by the outer air, and the airflow source (the airflow source 16 or the blade-type fan) is set at a place at a distance of 300 mm from the sensor. Then, the airflow source is operated for three (3) seconds and a response of the sensor of the thermal anemometer is measured. As shown in FIG. 8, after a signal is input to the airflow source, the sensor of the thermal anemometer shows its reaction after two (2) seconds in a case of the blade-type fan, and in contrast, the sensor shows the reaction after one (1) second in a case of the airflow source of the piezoelectric-type, and accordingly, it is possible to read a level of a static pressure producing ability of the piezoelectric-type airflow source 16. Furthermore, it can be understood that the wind velocity of the piezoelectric-type airflow source 16 is faster than that of the blade-type fan by approximately three (3) times.

In this embodiment, since the airflow source 16 utilizing the diaphragm 34 having the piezoelectric device 32 is employed, it is possible to produce a high static pressure in the fragrance chamber 14 in a short time period, whereby the fragrance cam be presented within a range extremely bounded in terms of space with excellent responsiveness. That is, a time-space-control by a single mechanism (airflow source) becomes possible. Furthermore, since the fragrance is presented within a range bounded in terms of space with excellent responsiveness, focusing on a pinpointed spot, not only the aromatic material to be used can be greatly saved but also a lingering fragrance hardly occurs. Because the aromatic material to be used may be a small quantity, it is possible to make the fragrance chamber 14 accommodating the fragrance source 20 smaller. Furthermore, no lingering fragrance occurs, and accordingly, a separate deodorization function becomes not needed.

Accordingly, according to this embodiment, the olfactory display 10 can be miniaturized. In a specific example, ultra-miniaturization up to a cube approximately 20 mm on each side can be implemented as a whole.

Furthermore, since the solid-like fragrance source 20 manufactured by soaking a liquid aromatic material into a granular porous material is used, it is possible to gradually release the aromatic material (fragrance component) from the fragrance source 20. That is, the fragrance source 20 can continuously release the fragrance component therefrom for a long period of time. Therefore, the olfactory display 20 can be used for a long period of time without refilling the liquid aromatic material to the fragrance source 20 or exchanging the fragrance source 20, and thus, an exchanging frequency of the fragrance source 20 can be reduced.

In addition, in the above-described embodiment, in order to use the fragrance source 20 in the fragrance chamber 14 with a good balance, the fragrance outlet 24 of the fragrance chamber 14 is formed in a direction intersecting orthogonally to the air inlet 26; however, positions that the fragrance outlet 24 and the emitting port 22 are to be formed are not restricted thereto and optional. Furthermore, an air passage within the fragrance chamber 14 from the air inlet 26 to the fragrance outlet 24 may be detoured by providing a partition in the fragrance chamber 14, for example. However, an attention is to be paid because the static pressure within the fragrance chamber 14 at a time of operation of the airflow source 16 becomes low if the air passage is made longer.

Furthermore, in the above-described embodiment, a manner that only a kind of fragrance is presented; however, two or more kinds of fragrances can be presented. For example, the olfactory display 10 shown in FIG. 3 is arranged in a plural number to set up an olfactory display system, and the fragrance sources 20 having different fragrances may be accommodated in the fragrance chambers 14 of the respective olfactory displays 10. In this case, it becomes possible to present to a user a different fragrance in synchronization with a change of a content displayed by an audio-visual display. For example, in accordance with a scene change of a video content, a fragrance of vanilla can be emitted in a scene that a vanilla ice cream is eaten, and a fragrance of the sea can be emitted in a scene of the beach.

Furthermore, by forming a plurality of fragrance chambers 14 in the housing 12, it is possible to present two or more kinds of fragrances by a single apparatus (olfactory display 10). In the following, with referring to FIGS. 9-12, an olfactory display 10 being another embodiment according to the present invention and capable of presenting a plurality of kinds of fragrances will be described; however, by applying the same reference numerals to the same or similar portions of the embodiment shown in FIG. 3, a duplicate description will be omitted or simplified. This is true for further embodiments described later. In addition, internal structure of the olfactory display 10 viewed from a side surface direction is shown in FIG. 3, but, in FIG. 9, internal structure of the olfactory display 10 viewed from above is shown.

Figure 9:
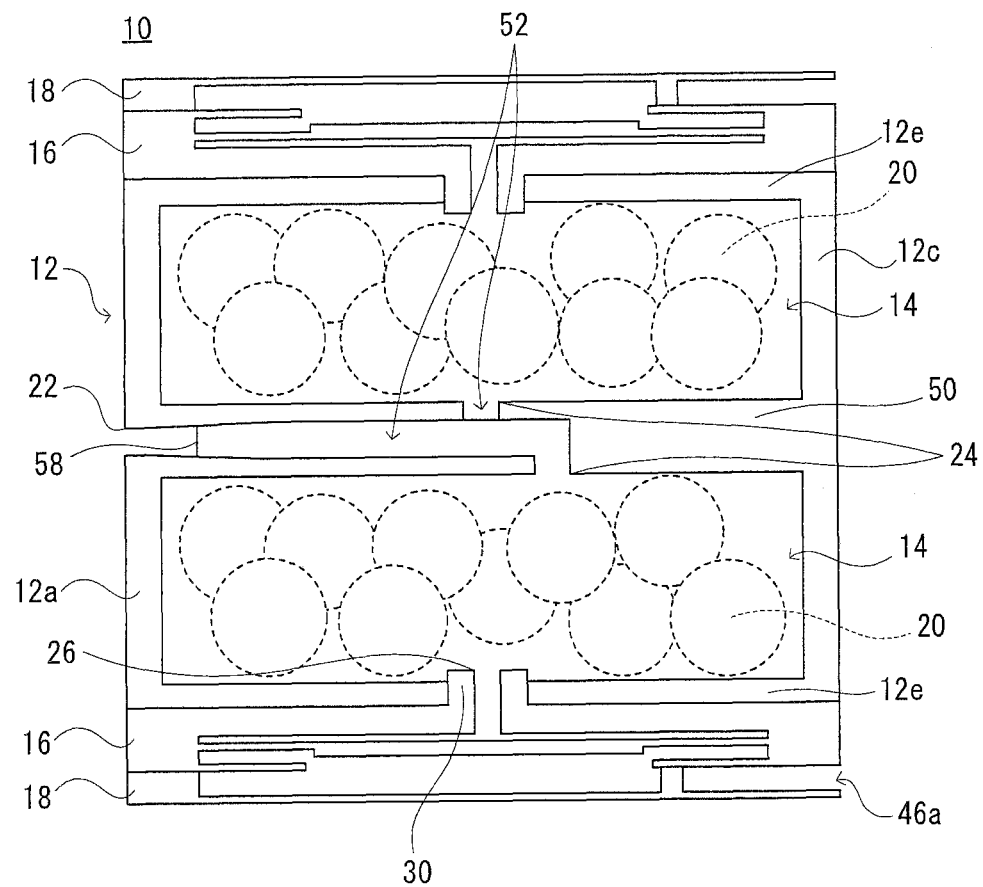
FIG. 9 is a view showing internal structure of an olfactory display which is another embodiment according to the present invention viewed from an upper direction.

As shown in FIG. 9, the olfactory display 10 is a ultrasmall olfactory display which is formed in a shape of a cube approximately 20 mm on each side, and comprises a housing 12, and a plurality of (two in this embodiment) fragrance chambers 14 formed by partitioning an internal space of the housing 12 by a partitioning wall 50. Each of the fragrance chambers 14 is provided with an airflow source 16 and an operation noise suppressing portion 18.

The housing 12 is formed in a shape of a rectangular parallelepiped by a suitable material such as an acrylic resin, a fluororesin, a stainless steel, etc., and an emitting port 22 is formed on a side wall 12a in a front side of the bhousing. An internal space of the housing 12 is partitioned into left and right by a plate-like partitioning wall 50 which connects the side wall 12a in the front side and a side wall 12c in a rear side, and within the housing 12, the fragrance chambers 14 which are two independent sealed spaces lining side by side are formed. A thickness of the partitioning wall 50 is 2.0 mm, for example, and a diameter of the emitting port 22 is 0.8 mm$\phi$, for example.

Solid-like fragrance sources 20 having different fragrances are accommodated in the fragrance chambers 14. In addition, although not shown, an opening for taking the fragrance source 20 in or out of the fragrance chamber 14 is formed on the side wall 12c in the rear side of the housing 12. The opening is properly sealed with using a sponge stopper or the like after the fragrance source 20 is accommodated.

Furthermore, in each of the fragrance chambers 14, there are formed with a fragrance outlet 24 and an air inlet 26. In this embodiment, a nozzle 30 of the airflow source 16 is connected to a side wall 12e of the housing 12 so as to be penetrated, and the nozzle 30 functions as the air inlet 26 by which an air is flown into the fragrance chamber 14. Furthermore, the fragrance outlets 24 are shifted in the front and rear direction, and communicated with the emitting port 22 via individual fragrance paths 52. In this embodiment, each of the fragrance paths 52 is a penetrating hole penetrating in the partitioning wall 50, and after extending from the fragrance outlet 24 up to a center portion in the thickness direction of the partitioning wall 50, extends toward the emitting port 22 while being bent. Each fragrance path 52 is formed in a circle shape in cross-section, and an inner diameter thereof is 1.0 mm$\Phi$, for example. In addition, a reason why the fragrance outlets 24 are arranged to be shifted in the front and rear direction is that if the fragrance outlets 24 are arranged at positions matching in the front and rear direction, the partitioning wall 50 becomes thin due to the fragrance path 52 extending from the fragrance outlet 24, which may result in an insufficient strength of the partitioning wall 50. However, if there is no problem in the strength of the partitioning wall 50, arranging positions of the fragrance outlet 24 are not restricted, especially. Thus, by forming the fragrance paths 52 by the penetrating holes penetrating in the partitioning wall 50, the olfactory display 10 can be miniaturized in comparison with a case that spaces for forming the fragrance paths 52 are separately prepared.

Figure 10:
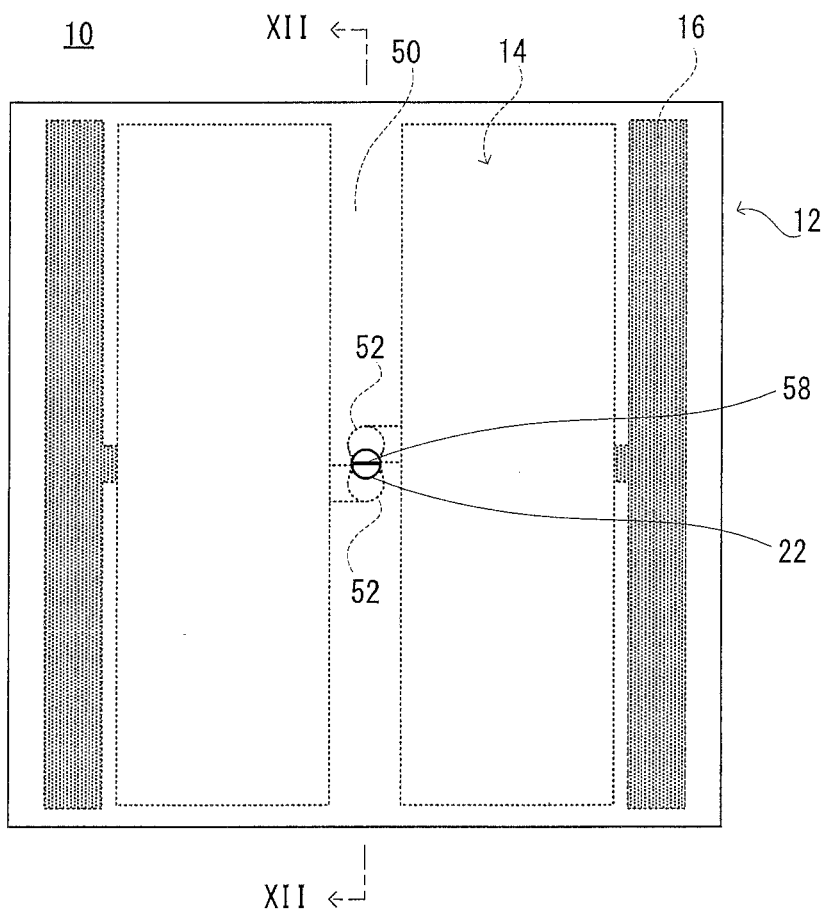
FIG. 10 is a view showing a shape of a fragrance path provided on the olfactory display in FIG. 9, and further schematically showing a situation that the olfactory display is viewed from a side of an emitting port as well as the internal structure.
Figure 11:
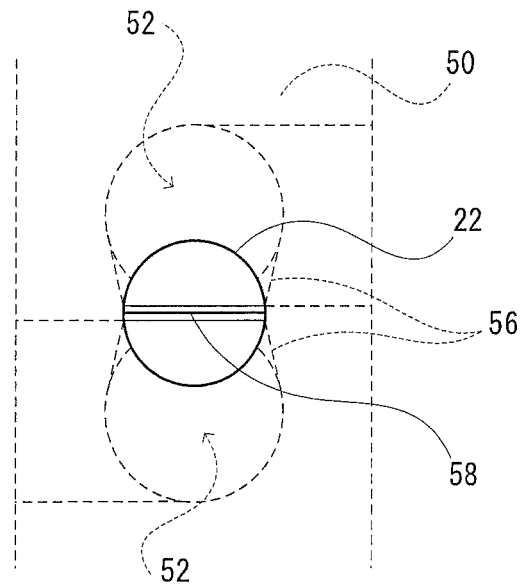
FIG. 11 is a view enlargedly showing a portion of the emitting port in FIG. 10.
Figure 12:
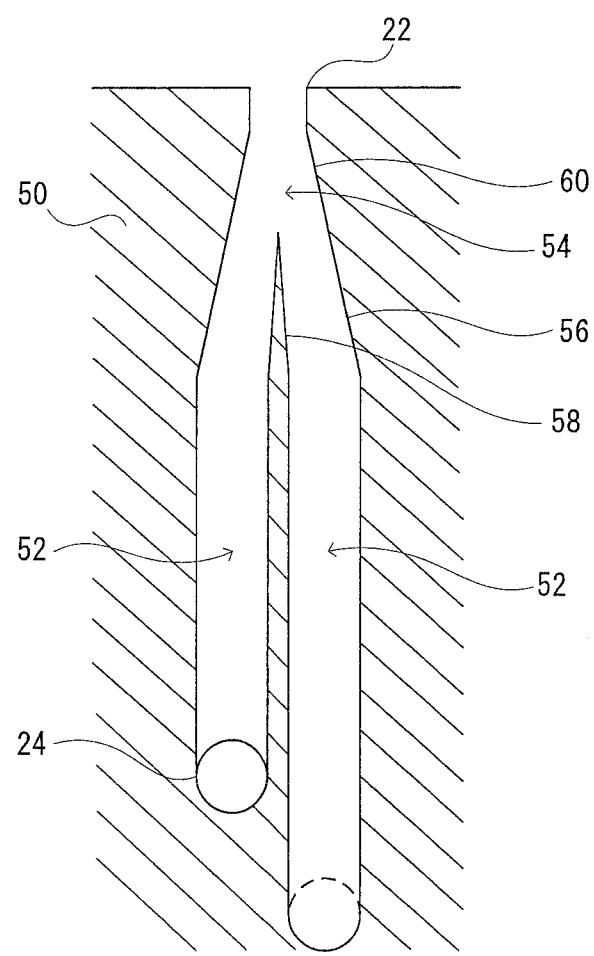
FIG. 12 is a cross-sectional view enlargedly showing a portion of the fragrance path in a cross-section cut-away at an XII-XII line in FIG. 10.

With referring to FIG. 10-FIG. 12, a shape of the fragrance path 52 will be described in more detail. The two fragrance paths 52 extend abreast in parallel with each other toward the emitting port 22, and then joined with each other at a position near the emitting port 22 to be rendered as a single common path 54 reaching the emitting port 22. In a joining portion 56, venturi tube structure is provided. In addition, the venturi tube structure means structure utilizing a venturi effect that by narrowing a fluid flow, a flowing speed is increased and thus a low pressure is produced.

In this embodiment, a flat-plate-like partitioning plate 58 is formed at the joining portion 56 of the fragrance paths 52. The partitioning plate 58 has a pointed shape toward the emitting port 22 such that an angle of a tip end is rendered five (5) degrees, for example, and functions as a guide plate for guiding the fragrance flowing into each of the fragrance paths 52 in a direction of the emitting port 22, whereby a backflow of the fragrance and an entry of the fragrance to another fragrance path 52 can be prevented. However, in a case where the partitioning plate 58 is thinly formed as a whole, it is not necessary to form the tip end thereof into a pointed shape.

At both sides of the partitioning plate 58, a cross-section area of the fragrance path 52 is made small. Furthermore, in the common path 54, the diameter-reduced portion 60 that a diameter of the common path is gradually reduced toward the emitting port 22 is formed. That is, in this embodiment, the joining portion 56 of the fragrance paths 52 has venturi tube structure in two portions, and accordingly, the flowing speed of the fragrance passing the joining portion 56 is accelerated in two phases.

As described above, the olfactory display 10 having such the structure presents to the user a content which is presented by a personal computer or the like and includes an image and sound by adding a fragrance to the content. A controller (not shown) of the olfactory display 10 applies an alternating voltage to the piezoelectric device 32 of the corresponding airflow source 16 in response to an instructing signal sent from the personal computer or the like. If the diaphragm 34 is bent and vibrated due to the application of the alternating voltage, an air is sucked from the air port 46a of the operation noise suppressing portion 18, and a high speed and high pressure air is sent into the fragrance chamber 14 from the nozzle 30 of the airflow source 16, that is, from the air inlet 26. A gas-like fragrance component volatilized from the fragrance source 20 is included in the air within the fragrance chamber 14, and the air (fragrance) including such a fragrance component passes from the individual fragrance path 52 and reaches the common path 54 to be emitted from the emitting port 22. Then, if the application of the alternating voltage to the piezoelectric device 32 is stopped, the emission of the fragrance from the emitting port 22 is also stopped. At this time, since the piezoelectric-type airflow source 16 is utilized, the start and stop of the emission of the fragrance is performed with excellent responsiveness (that is, a precise temporal control is possible), and further, the presentation of a continuous and constant fragrance not being pulsative is also possible. Furthermore, since there is provided with the venturi tube structure (the partitioning plate 58 and the diameter-reduced portion 60) at the joining portion 56 of the fragrance paths 52, a velocity of the fragrance passing the joining portion 56 is sufficiently accelerated, whereby not only an adhesion of the fragrance component (lingering fragrance) at the joining portion can be prevented but also the fragrance can be emitted from the emitting port with a higher directivity.

In addition, when the olfactory display 10 shown in FIG. 9 is practically operated, it is confirmed that an operation performance (time-space-controllability, deodorization ability, repeatedly usability, etc.) similar to that of the embodiment shown in FIG. 3 is shown.

According to the embodiment shown in FIG. 9, even in a case where a plurality of fragrance chambers 14 are provided in the housing 12, as similar to the embodiment shown in FIG. 3, it is possible to present a fragrance within a range extremely bounded in terms of space with an excellent responsiveness, and the apparatus itself can be miniaturized.

In the embodiment shown in FIG. 9, since the two fragrance chambers 14 are provided in the housing 12, by accommodating fragrance sources 20 having different fragrances in the respective fragrance chambers 14, it is possible to present two kinds of fragrances individually. Accordingly, it becomes possible to present to the user a different fragrance in synchronization with a change of a content displayed by the audio-visual display.

Furthermore, since the common path 54 that the fragrance paths 52 are joined at a position near the emitting port 22 so as to emit a fragrance from a single emitting port 22, by simultaneously or in a time-shared manner operating the airflow sources 16 of the fragrance chambers 14, it becomes possible to present a compound or mixed fragrance. Furthermore, by adjusting a duty ratio of the input signal to each of the airflow sources 16, for example, it is possible to appropriately change a ratio of a fragrance to be compounded or mixed.

In addition, in an olfactory display system in which the olfactory display 10 shown in FIG. 3 is arranged abreast in a plural number, fragrances are emitted from respective emitting ports 22. Therefore, in order to spatially control the fragrances toward a nose of the user, it is necessary to perform individual adjustment (calibration) for each olfactory display 10. Furthermore, fragrances cannot be compounded or mixed. In contrast, in the olfactory display 10 shown in FIG. 9, since a plurality of fragrances can be presented from a single emitting port 22, the adjustment for a space-control is easy and fragrances can be compounded or mixed.

Furthermore, since there is provided with the venturi tube structure in the joining portion 56 of the fragrance paths 52, a velocity of the fragrance passing the joining portion 56 can be sufficiently increased, whereby an adhesion of the fragrance component at the joining portion can be prevented, that is, an undesired mix of the fragrances can be prevented, and the fragrance can be emitted from the emitting port 22 with a higher directivity.

In addition, in the embodiment shown in FIG. 9, the two fragrance chambers 14 are arranged in the horizontal direction, but two fragrance chambers 14 may be arranged in the vertical direction. Furthermore, although the airflow source 16 is provided so as to penetrate the side wall 12*e* of the housing 12, a side surface of the fragrance chamber 14 can be sealed by the top plate 44 of the airflow source 16 without providing the side wall 12*e*. That is, it is possible to function the airflow source 16 as a part of an outer wall of the housing 12.

In addition, in the embodiment shown in FIG. 9, although the fragrance path 52 is formed by a penetrating hole penetrating the partitioning wall 50, not limited to such structure. For example, a space is formed in the partitioning walls 50 partitioning the fragrance chambers 14 and the fragrance path 52 may be formed by an independent tube passing through the space.

Furthermore, a position of the fragrance outlet 24, a shape and route of the fragrance path 52 and so on can be arbitrarily changed. For example, in the embodiment shown in FIG. 9, the fragrance path 52 is formed in a circle shape in cross-section, but the fragrance path 52 may be formed in a semi-circle shape in cross-section, a fanwise shape in cross-section or the like. In such a case, it is preferable to form a plurality of individual fragrance paths 52 in a semi-circle shape in cross-section, a fanwise shape in cross-section or the like by partitioning an internal of the air passage of the circle shape in cross-section by a plane-plate-like partition. In addition, if the fragrance path 52 is made longer and/or to have a number of bends, it may result in that a static pressure of the fragrance chamber 14 at a time of the operation of the airflow source 16 becomes unfavorably low, and therefore, it is preferable that the fragrance path 52 is formed so as to be short and to have less bends.

Furthermore, in the embodiment shown in FIG. 9, although the fragrance source 20 is accommodated in each of the fragrance chambers 14, not limited to this manner. One of the fragrance chambers 14 may not be accommodated with the fragrance source 20, may be accommodated with only a granular body to which no fragrance component is added, e.g., a porous material into which no liquid aromatic material is soaked or only a non-porous granular body, or may be made as an empty chamber that nothing is accommodated. In such cases, after the fragrance is presented by operating the airflow source 16 of the fragrance chamber 14 in which the fragrance source 20 is accommodated, by operating the airflow source 16 of the fragrance chamber 14 not accommodated with the fragrance source 20, an odorless air is emitted. According to this, a density of the fragrance component in a space surrounding a nose of the user can be lowered immediately to a density below a threshold value that the user perceives, and accordingly, a quicker deodorization becomes possible in comparison with a case that the fragrance component is freely diffused as it is. Furthermore, similar to a case where fragrances are compounded or mixed, the density of the fragrance component can be adjusted by operating simultaneously or in a time-shared manner the airflow source 16 of the fragrance chamber 14 accommodated with the fragrance source 20 and the airflow source 16 of the fragrance chamber 14 not accommodated with the fragrance source 20.

Furthermore, a deodorization agent may be accommodated in one of the fragrance chambers 14. According to this, a quicker deodorization after the presentation of the fragrance becomes possible.

In addition, in the embodiment shown in FIG. 9, the two fragrance chambers 14 are provided; however, the number of the fragrance chambers 14 may be arbitrarily set, and therefore, it is possible to provide three or more fragrance chambers 14. As an embodiment shown in FIG. 13, for example, four fragrance chambers 14 may be provided. In the following, with referring to FIG. 13 and FIG. 14, an olfactory display 10 which is a further embodiment according to the present embodiment will be described.

Figure 13:
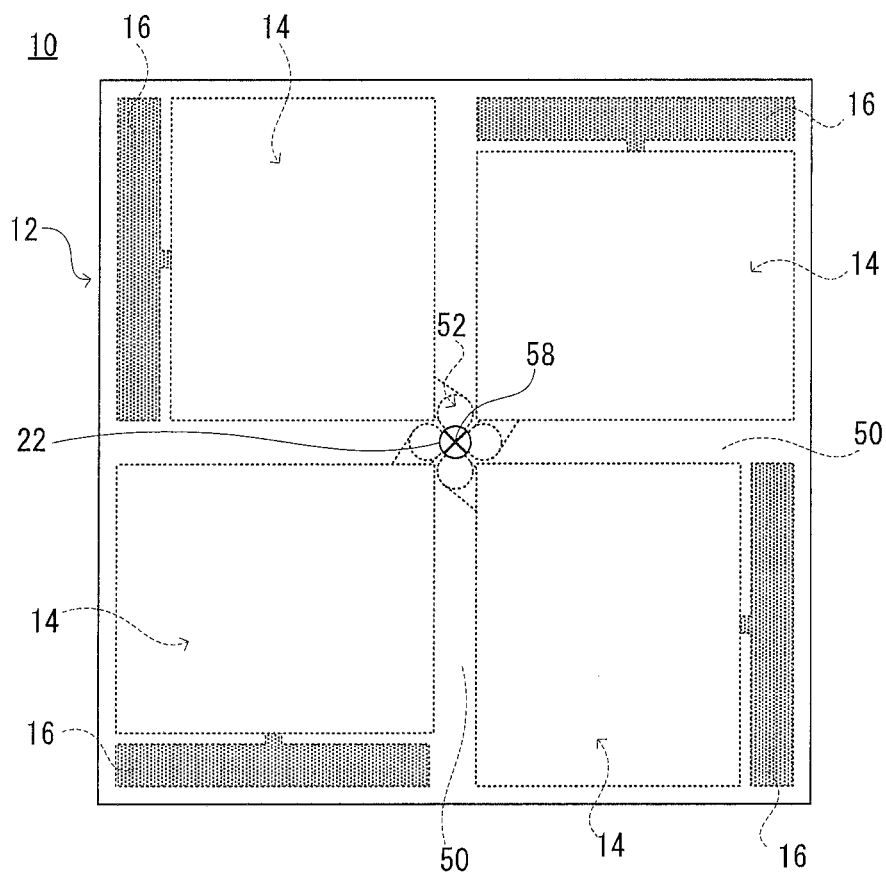
FIG. 13 is a view schematically showing a situation that an olfactory display which is a further embodiment according to the present invention is viewed from a side of an emitting port as well as internal structure thereof.
Figure 14:
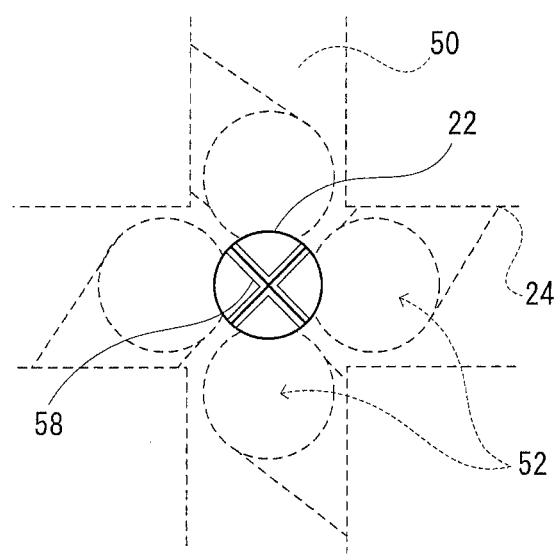
FIG. 14 is a view enlargedly showing a portion of the emitting port in FIG. 13.

As shown in FIG. 13 and FIG. 14, an emitting port 22 is formed on a side wall 12*a* of a housing 12 in a front side. An internal space of the housing 12 is partitioned in the horizontal and vertical directions by partitioning walls 50 which are a crosswise in cross-section and connects the side wall 12a in the front side and a side wall 12c in a rear side, whereby four fragrance chambers 14 each of which is an independent sealed space are formed within the housing 12. In the fragrance chambers 14, solid-like fragrance sources 20 having fragrances different from each other are accommodated. In each of the fragrance chambers 14, an airflow source 16 and an operation noise suppressing portion 18 are provided.

Respective fragrance outlets 24 of the fragrance chambers 14 are communicated with the emitting port 22 via individual fragrance paths 52. The fragrance paths 52 extend toward the emitting port 22 in parallel with each other and bent after extended up to a center portion in the thickness direction of the partitioning walls 50 from the fragrance outlets 24. Then, the four fragrance paths 52 are jointed to each other at a position near the emitting port 22 to be rendered as a single common path 54 reaching the emitting port 22. A partitioning plate 58 functioning as a guide plate is provided in a joining portion 56 of the fragrance paths 52. The partitioning plate 58 has a shape that plane plates are intersected orthogonally to each other, and a tip end thereof is formed into a pointed shape. Furthermore, in the common path 54, a diameter-reduced portion 60 that a diameter of the common path 54 is gradually reduced toward the emitting port 22 is formed. That is, in the embodiment shown in FIG. 13 and FIG. 14, the venturi tube structure is formed in two portions in the joining portion 56 of the fragrance paths 52, and therefore, a flowing speed of the fragrance passing the joining portion 56 can be accelerated in two phases.

In the olfactory display 10 shown in FIG. 13, since four kinds of fragrance sources 20 are used, on the assumption that the fragrance sources 20 of the fragrance chambers 14 are A, B, C and D, for example, the number of kinds of the fragrance to be presented by compounding or mixing the fragrances such as "A+B, A+C, - - - , B+C+D, A+B+C+D" can be increased remarkably.

In addition, as similar to the embodiment shown in FIG. 9, one of the fragrance chambers 14 may not be accommodated with the fragrance source 20, or may be accommodated with a deodorization agent. Furthermore, in a case where a number of the fragrance chambers 14 are provided, two or more fragrance chambers 14 not accommodated with the fragrance sources 20 or accommodated with deodorization agents may be provided. Furthermore, it is possible to be provided with both of the fragrance chamber 14 not accommodated with the fragrance source 20 and the fragrance chamber 14 accommodated with the deodorization agent.

Figure 15:
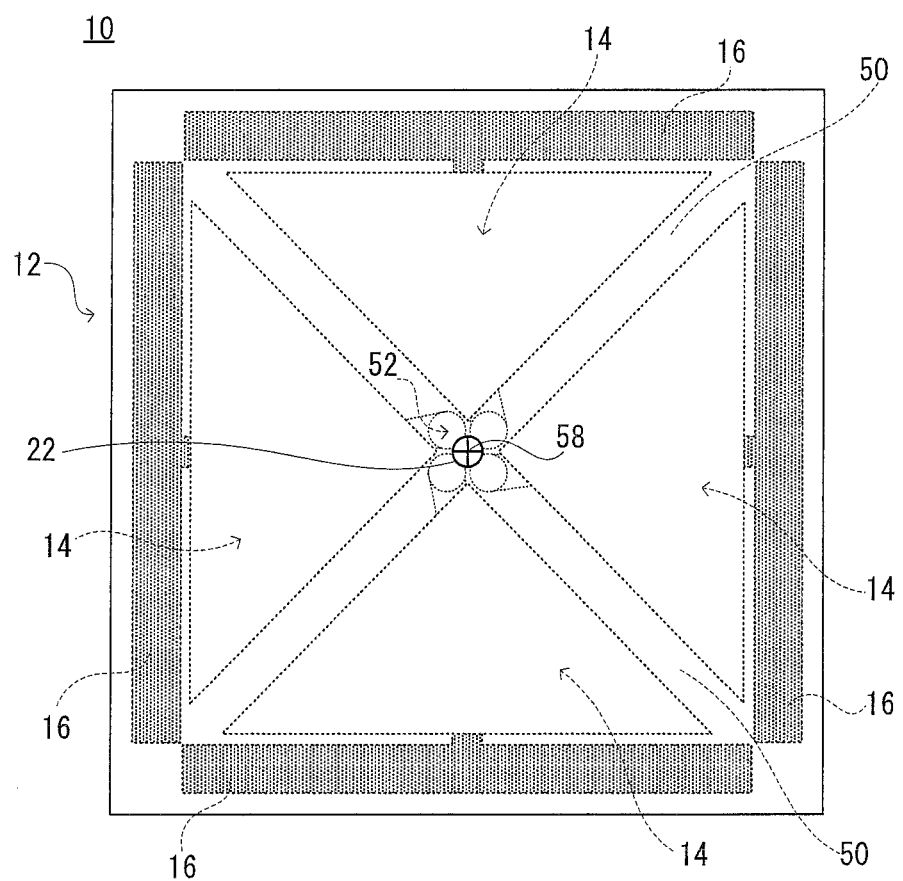
FIG. 15 is a view schematically showing a situation that an olfactory display which is a still further embodiment according to the present invention is viewed from a side of an emitting port as well as internal structure thereof.

An arranging manner of the fragrance chambers 14 and the airflow sources 16 is arbitrarily changeable, and as shown in FIG. 15, it is possible to form fragrance chambers 14 by partitioning an internal space of the housing 12 in the horizontal and vertical directions by partitioning walls 50 of a crosswise shape in cross-section and extending in a manner of diagonal line manner. By arranging the fragrance chambers 14 and the airflow sources 16 as shown in FIG. 15, it is possible to secure a large arranging space of the airflow source 16 while the olfactory display 10 is not being large-sized. In addition, in a case where a size of each of the fragrance chambers 14 becomes too small by providing a number of the fragrance chambers 14, by making a length in a front-rear direction of the housing 12 longer, a size of each of the fragrance chambers 14 can be adjusted.

Figure 16:
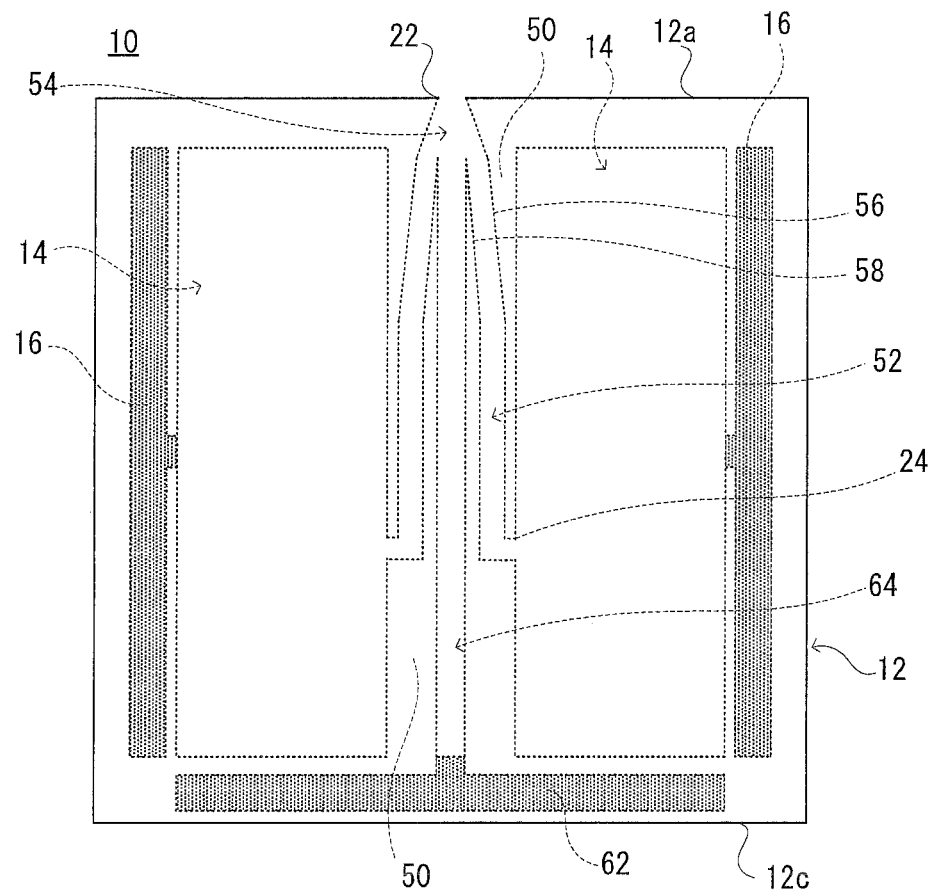
FIG. 16 is a view schematically showing a situation that an olfactory display which is the other embodiment according to the present invention is viewed from a side of an emitting port as well as internal structure thereof.

In addition, in an olfactory display 10 comprising a plurality of fragrance chambers 14 as shown in the above-described FIG. 9-FIG. 15, as the number of the fragrance chambers 14 to be provided becomes larger, a shape of the joining portion 56 of the fragrance paths 52 becomes complex. Accordingly, it may cause a drop in the pressure and thus an unfavorably poor emission performance of the fragrance. Therefore, an auxiliary airflow source 62 may be provided in the housing 12 separately from the airflow sources 16 provided in the fragrance chambers 14. In the following, with referring to FIG. 16 and FIG. 17, an olfactory display 10 which comprises an auxiliary airflow source 62, being a further embodiment according to the present invention will be described. FIG. 16 is a view schematically showing a situation that the olfactory display 10 is viewed from the upper direction together with internal structure thereof, and FIG. 17 is a view enlargedly showing a situation that a portion of an emitting port 22 is viewed from a side of an emitting port 22.

Figure 17:
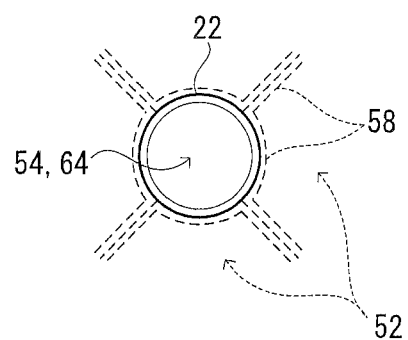
FIG. 17 is a view enlargedly showing a situation that the emitting port of FIG. 16 is viewed from a side of an emitting port.

The olfactory display 10 shown in FIG. 16 and FIG. 17 is, as similar to the embodiment shown in FIG. 15, provided with four fragrance chambers 14 by partitioning in internal space of a housing 12 in the horizontal and vertical directions with partitioning walls 50 extending in a shape of diagonal lines and having a crosswise shape in cross-section. Airflow sources 16 are provided in the fragrance chambers 14, and the airflow sources 16 are arranged on the left and right side surface portions and upper and lower surface portions of the housing 12. In each of the airflow sources 16, an operation noise suppressing portion 18 is suitably provided. An emitting port 22 is formed on a side wall 12a of the housing 12 in a front side. Four fragrance paths 52 extending from fragrance outlets 24 of the fragrance chambers 14 are joined with each other at a position near the emitting port 22 so as to be rendered as a single common path 54 reaching the emitting port 22.

Furthermore, in this embodiment, an auxiliary airflow source 62 is provided on a side wall 12c in a rear side of the housing 12, and the auxiliary airflow source 62 is independent from the fragrance chambers 14, that is, not directly connected to internals of the fragrance chambers 14. It is preferable that an object similar to the airflow source 16, that is, an object which comprises a diaphragm onto which a piezoelectric device is adhered and generates an airflow by vibrating the diaphragm when an alternating voltage is applied to the piezoelectric device is used as the auxiliary airflow source 62. An operation noise suppressing portion 18 is properly provided to the auxiliary airflow source 62. Furthermore, in the partitioning walls 50 of the housing 12, there is formed with an auxiliary path 64 which becomes a passage of an air (odorless air) discharged from a nozzle of the auxiliary airflow source 62. The auxiliary path 64 is a penetrating hole which communicates the nozzle of the auxiliary airflow source 62 and a common path 54 with each other in a straight line manner, and the auxiliary path 64 is joined to the common path 54 passing a central portion of the partitioning walls 50, i.e., the partitioning walls 50 partitioning four fragrance paths 52 and a center portion of the partitioning plate 58 so as to be united to the common path 54, extending up to the emitting port 22 in a straight line manner.

In the olfactory display 10 of the embodiment shown in FIG. 16, if the auxiliary airflow source 62 is operated, an odorless air is discharged from the nozzle of the auxiliary airflow source 62 into the auxiliary path 64. The odorless air flows straight up to the emitting port 22 without moving forward a complex path and accordingly, the odorless air is emitted from the emitting port 22 without generating a drop of the pressure.

In presenting a fragrance to the user by the embodiment shown in FIG. 16, the airflow source 16 provided in the fragrance chamber 14 in which a target fragrance source 20 is accommodated is operated, and at the same time or in a time-shared manner, an auxiliary airflow source 62 is operated. Then, a fragrance toward the emitting port 22 passing through the fragrance path 52 is joined to the odorless air discharged from the auxiliary airflow source 62 in the common path 54 to be accelerated and vigorously emitted from the emitting port 22 with a higher straightness.

According to the embodiment shown in FIG. 16, because the auxiliary airflow source 62 is provided, the presentation of the fragrance having more excellent directivity is made possible. Especially, in a case where a number of the fragrance chambers 14 are provided, such an advantage is remarkable. Furthermore, since a stay of the fragrance in the common path 54 can be more effectively suppressed, it is possible to more effectively prevent an adhesion of the fragrance component to the common path 54.

Furthermore, according to the embodiment shown in FIG. 16, a density control of the fragrance component is also possible by changing a driving ratio of the airflow source 16 and the auxiliary airflow source 62 so as to adjust a mixing ratio of the fragrance and the odorless air. If the fragrance component is diffused or diluted by operating the auxiliary airflow source 62 to discharge the odorless air after the fragrance is presented by operating the airflow source 16 provided in the fragrance chamber 14, a quicker deodorization also becomes possible.

In addition, a discharging performance (static pressure producing ability) of the airflow source 16 and the discharging performance of the auxiliary airflow source 62 may be made to the same degree; however, it is possible to heighten the discharging performance of the auxiliary airflow source 62 than the discharging performance of the airflow source 16. By thus heightening the discharging performance of the auxiliary airflow source 62 than the discharging performance of the airflow source 16, it is possible to extend a distance of the presentation of the fragrance. That is, it is possible to convey the fragrance to a further point.

In order to heighten the discharging performance of the auxiliary airflow source 62, it is preferable that the auxiliary airflow source 62 which comprises a piezoelectric device having a diameter larger than that of the airflow source 16 is used, or that the auxiliary airflow source 62 which comprises a piezoelectric device two or more layered in a multi-layered arrangement is used. Furthermore, in a case where the same object is used for the airflow source 16 and the auxiliary airflow source 62, for example, the discharging performance of the auxiliary airflow source 62 may be heightened by making the alternating voltage applied to the piezoelectric device provided on the auxiliary airflow source 62 larger. Showing a specific example, the alternating voltage of 19.5 Vp-p is applied to the piezoelectric device 32 provided on the airflow source 16 while the alternating voltage of 30.0 Vp-p may be applied to the piezoelectric device provided on the auxiliary airflow source 62. However, if the alternating voltage to be applied to the piezoelectric device is made larger, it may cause a problem in a durability of the auxiliary airflow source 62, and accordingly, in such a case, it is preferable that a continuous driving of the auxiliary airflow source 62 is refrained and an intermittent driving for three (3) seconds, for example, is performed.

Furthermore, in the embodiment shown in FIG. 16, the auxiliary airflow source 62 is arranged in the rear side of the housing 12; however, an arranging position of the auxiliary airflow source 62 is not especially restricted, and is properly changeable in accordance with an arranging manner of the fragrance chambers 14 and the airflow sources 16 and so on. However, since it is preferable that the auxiliary path 64 is extended in a straight line manner from the auxiliary airflow source 62 to the emitting port 22, it is preferable that the auxiliary airflow source 62 is provided in the rear side of the housing 12. Furthermore, in the embodiment shown in FIG. 16, the auxiliary path 64 is rendered as a penetrating hole penetrating the partitioning walls 50, but not limited to such structure. In a case where a space is formed in the partitioning walls 50 partitioning the fragrance chambers 14 and the fragrance paths 52 are formed by an independent tube passing through the space, the auxiliary path 64 may be formed by an independent tube. Furthermore, a plurality of auxiliary airflow sources 62 may be provided on the housing 12.

In addition, in the embodiments shown in FIG. 9-FIG. 17, the venturi tube structure is provided in the joining portion 56 of the fragrance paths 52, but it is not necessary to provide the venturi tube structure.

The olfactory display 10 is formed in a cube-shape, but not limited thereto, and the olfactory display 10 can be formed into a suitable shape such as a rectangular parallelepiped shape, a polygonal column shape, a circle column shape, etc.

Furthermore, in the above-described embodiments, as the solid-like fragrance source 20, an object that a liquid aromatic material is soaked into a granular porous material is used, but not limited to such an object. For example, after a liquid aromatic material is dissolved in a base material, which is a solid or gel-like at normal temperature, liquefied by heating, the material is cooled at a normal temperature so as to solidify or gelate, and then, the material can be used as the solid-like fragrance source 20. However, in view of a point that a manufacture is simple and cheap and a point that a liquid aromatic material can be refilled, it is preferable that an object that a liquid aromatic material is soaked in a porous material is used as the solid-like fragrance source 20.

Furthermore, in the above-described embodiments, the olfactory display 10 is fixedly settld to emit a fragrance toward only one direction, but not limited to such a manner, and the olfactory display 10 can be set such that an emitting direction is changeable. For example, the olfactory display 10 can be set on a pedestal which supports the olfactory display 10 to be rotatable in the horizontal direction and the vertical direction. In such a case, it is preferable that a fragrance is presented by automatically tracing the nose of the user by combining with a device which detects the nose of the user.

Furthermore, in the above-described embodiments, a fragrance is presented in cooperation with audio-visual information, but a fragrance can be presented independently. For example, the olfactory display 10 is utilized as an apparatus for preventing dozing while driving that in a vehicle such as a car, for example, a dozing state of a driver is detected based on a face image, and in response to such a detection, a fragrance (an irritant odor) is emitted toward the nose of the driver. The olfactory display 10 can present a fragrance with respect to a range extremely bounded in terms of space, that is, has the directivity, and accordingly, the irritant odor can be presented only to the driver without affecting another person in the same car. Furthermore, in the olfactory display 10 capable of presenting two or more kinds of fragrances as shown in FIG. 9-FIG. 17, a different fragrance can be presented in accordance with a temperature, a humidity and the weather of that day, for example.

Although the present invention has been described and illustrated in detail, it is clearly understood that the same is by way of illustration and example only and is not to be taken by way of limitation, the spirit and scope of the present invention being limited only by the terms of the appended claims.

DESCRIPTION OF REFERENCE NUMERALS

10 denotes olfactory display;
12 denotes housing;

14 denotes fragrance chamber;
16 denotes airflow source(s);
18 denotes operation noise suppressing portion;
20 denotes fragrance source;
22 denotes emitting port;
24 denotes fragrance outlet;
26 denotes air inlet;
32 denotes piezoelectric device;
34 denotes diaphragm;
50 denotes partitioning wall(s);
52 denotes fragrance path(s);
54 denotes common path;
56 denotes joining portion of fragrance paths;
58 denotes partitioning plate;
60 denotes diameter-reduced portion;
62 denotes auxiliary airflow source; and
64 denotes auxiliary path.

The invention claimed is:

1. An olfactory display presenting a fragrance within a range bounded in terms of time and space, comprising:
 a housing having an emitting port;
 a fragrance chamber formed in the housing, the fragrance chamber having an air inlet and a fragrance outlet which is communicated with the emitting port;
 a solid-like fragrance source accommodated in the fragrance chamber;
 an airflow source which sends an air from the air inlet into the fragrance chamber by using a diaphragm having a piezoelectric device; and
 an operation noise suppressing portion provided at a side of an upper stream of the airflow source.

2. An olfactory display according to claim 1, wherein the fragrance outlet is formed in a direction intersecting orthogonally to the air inlet.

3. An olfactory display according to claim 1, further comprising:
 a plurality of fragrance chambers formed by partitioning an internal space of the housing by partitioning walls; and
 a plurality of fragrance paths extending toward the emitting port from respective fragrance outlets formed in the plurality of fragrance chambers, wherein
 the fragrance source is accommodated in at least one of the plurality of fragrance chambers,
 the airflow source is provided in each of the plurality of fragrance chambers, and
 the plurality of fragrance paths are joined to each other at a position near the emitting port to form a single common path.

4. An olfactory display according to claim 3, further comprising venturi tube structure in a portion that the plurality of fragrance paths are joined to each other.

5. An olfactory display according to claim 3, wherein the fragrance path is formed by a penetrating hole passing through an internal of the partitioning wall.

6. An olfactory display according to claim 4, wherein the venturi tube structure includes a diameter-reduced portion formed by reducing a diameter of the common path toward a side of the emitting port.

7. An olfactory display according to claim 4, wherein the venturi tube structure includes a partitioning plate provided at the joining portion of the plurality of fragrance paths.

8. An olfactory display according to claim 3, wherein at least one of the fragrance chambers is accommodated with a granular body into which no fragrance component is soaked as the fragrance source.

9. An olfactory display according to claim 3, wherein at least one of the fragrance chambers is rendered as an empty chamber.

10. An olfactory display according to claim 3, further comprising:
 an auxiliary airflow source provided with a diaphragm having a piezoelectric device; and
 an auxiliary path which communicates the auxiliary airflow source and the common path.

11. An olfactory display according to claim 10, wherein a discharging performance of the auxiliary airflow source is rendered higher than a discharging performance of the airflow source.

12. An olfactory display which presents a fragrance within a range bounded in terms of time and space, comprising:
 a housing having an emitting port;
 a plurality of fragrance chambers formed by partitioning an internal space of the housing with the partitioning walls, each fragrance chamber having an air inlet and a fragrance outlet;
 a solid-like fragrance source accommodated in at least one of the fragrance chambers;
 a plurality of airflow sources each of which is provided in each of the fragrance chambers and sends an air from the air inlet into the fragrance chamber by using a diaphragm provided with a piezoelectric device; and
 a plurality of fragrance paths each extending from the fragrance outlets toward the emitting port, wherein
 the plurality of fragrance paths are joined to each other in a position near the emitting port to form a single common path and venturi tube structure is formed at the joining portion.

* * * * *